US012758498B2

(12) United States Patent
Devarakonda et al.

(10) Patent No.: US 12,758,498 B2
(45) Date of Patent: Oct. 13, 2026

(54) TOPICAL GEL FORMULATION FOR SKIN AND MOUTH DISORDERS AND A PROCESS OF PREPARATION THEREOF

(71) Applicants: Ramakrishna Devarakonda, Twin Oaks, MO (US); Ashok Chandra Illapakurthy, Belle Mead, NJ (US)

(72) Inventors: Ramakrishna Devarakonda, Twin Oaks, MO (US); Ashok Chandra Illapakurthy, Belle Mead, NJ (US)

( * ) Notice: Subject to any disclaimer, the term of this patent is extended or adjusted under 35 U.S.C. 154(b) by 160 days.

(21) Appl. No.: 18/720,669

(22) PCT Filed: Dec. 16, 2022

(86) PCT No.: PCT/IB2022/062351

§ 371 (c)(1),
(2) Date: Jun. 17, 2024

(87) PCT Pub. No.: WO2023/111971

PCT Pub. Date: Jun. 22, 2023

(65) Prior Publication Data

US 2025/0049708 A1 Feb. 13, 2025

(30) Foreign Application Priority Data

Dec. 17, 2021 (IN) ............................. 202141058855

(51) Int. Cl.

| | |
|---|---|
| ***A61K 9/06*** | (2006.01) |
| ***A61K 9/00*** | (2006.01) |
| ***A61K 31/5575*** | (2006.01) |
| ***A61K 47/10*** | (2017.01) |
| ***A61P 1/02*** | (2006.01) |

(52) U.S. Cl.
CPC .............. *A61K 9/06* (2013.01); *A61K 9/0014* (2013.01); *A61K 9/006* (2013.01); *A61K 31/5575* (2013.01); *A61K 47/10* (2013.01); *A61P 1/02* (2018.01)

(58) Field of Classification Search
None
See application file for complete search history.

(56) References Cited

U.S. PATENT DOCUMENTS

| | | | |
|---|---|---|---|
| 5,510,384 | A | 4/1996 | McKee et al. |
| 6,656,503 | B1 | 12/2003 | Sherman |
| 2009/0088366 | A1 | 4/2009 | Garvey |
| 2016/0331735 | A1 | 11/2016 | Latif |

FOREIGN PATENT DOCUMENTS

| | | | | |
|---|---|---|---|---|
| CN | 106667900 A * | 5/2017 | | ............... A61K 9/06 |
| WO | 2008120264 A1 | 10/2008 | | |

* cited by examiner

*Primary Examiner* — Brian J Davis

(57) ABSTRACT

The invention relates to a formulation of topical or oromucosal gel for the treatment of disorders of skin and mouth. The formulation comprises misoprostol 1% dispersion, mineral oil, PEG 400-Part I. PEG 400-Part II and PEG 3350. The invention discloses formulations of two gels comprising 100 ug/g of misoprostol drug corresponding to a concentration of 0.01% and 30 ug of misoprostol drug corresponding to a concentration of 0.003% respectively. The formulation is effective against oral mucositis. RAS, diabetes foot ulcers, decubitus ulcers and skin burns. The animal studies indicate reduction of oral mucositis upon administration of the drug along with decrease in levels of biomarkers IL-6 and TNF-α and the body weight has been significantly maintained which indicate the drug to be safe and effective.

9 Claims, 10 Drawing Sheets

| Product | | 0.01% MISOPROSTAL D. CREAM (100 µg/g) | | | 0.003% MISOPROSTAL D. CREAM (30 µg/g) | | |
|---|---|---|---|---|---|---|---|
| Sl. No. | Composition | MST-044-037 | | | MST-044-040 | | |
| | Ingredients | mg/ g | %w/w | g/batch | mg/ g | %w/w | g/batch |
| 1 | Misoprostol 1% dispersion | 10.00 | 1.00 | 2.50 | 3.00 | 0.30 | 0.75 |
| 2 | Mineral Oil | 100.00 | 10.00 | 25.00 | 100.00 | 10.00 | 25.00 |
| 3 | Polyethylene Glycol 400 - Part I | 100.00 | 10.00 | 25.00 | 100.00 | 10.00 | 25.00 |
| | Polyethylene Glycol 400 - Part II | 464.40 | 26.44-66.44 | 116.10 | 464.40 | 26.44-66.44 | 116.10 |
| 4 | Polyethylene Glycol 3350 | 325.60 | 12.56-52.56 | 81.40 | 332.60 | 13.26-53.26 | 83.15 |
| | Total weight | 1000.00 | 100.00 | 250.00 | 1000.00 | 100.00 | 250.00 |

FIGURE 1

| Product | | 0.01% MISOPROSTAL D. CREAM (100ug/g) | | | 0.003% MISOPROSTAL D. CREAM (30ug/g) | | |
|---|---|---|---|---|---|---|---|
| Sl. No. | Composition | MST-044-037 | | | MST-044-040 | | |
| | Ingredients | g/ 100g | %w/w | g/batch | g/ 100g | %w/w | g/batch |
| 1 | Misoprostol 1% dispersion | 1.00 | 1.00 | 2.50 | 0.30 | 0.30 | 0.75 |
| 2 | Mineral Oil | 10.00 | 10.00 | 25.00 | 10.00 | 10.00 | 25.00 |
| 3 | Polyethylene Glycol 400 - Part I | 10.00 | 10.00 | 25.00 | 10.00 | 10.00 | 25.00 |
| | Polyethylene Glycol 400 - Part II | 46.44 | 26.44-66.44 | 116.10 | 46.44 | 26.44-66.44 | 116.10 |
| 4 | Polyethylene Glycol 3350 | 32.56 | 12.56-52.56 | 81.40 | 33.26 | 13.26-53.26 | 83.15 |
| | Total weight | 100.00 | 100.00 | 250.00 | 100.00 | 100.00 | 250.00 |

FIGURE 2

| Mucositis Score | Parameter |
|---|---|
| 0 | Completely healthy cheek pouch with no erosion or vasodilation |
| 1 | Presence of erythema, but no evidence of erosion in the cheek pouch |
| 2 | Severe erythema, vasodilation and surface erosion |
| 3 | Formation of ulcers in one or more faces of the mucosa, but not affecting 25% of the surface area of the check pouch, as well as severe erythema and vasodilation |
| 4 | Cumulative formation of ulcers of about 50% of the surface area of cheek pouch |
| 5 | Complete ulceration of the cheek pouch mucosa, in which the fibrosis makes oral mucosa exposure difficult |

FIGURE 4

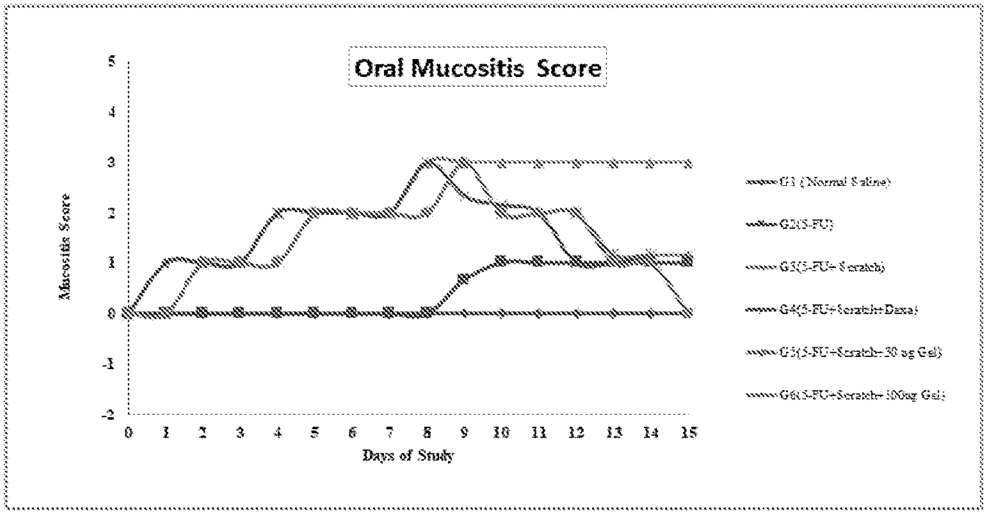

FIGURE 5

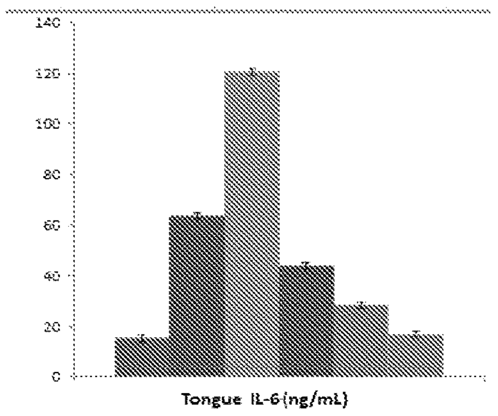
FIGURE 6
| Tongue IL-6 (ng/mL) | | |
|---|---|---|
| Group | Mean Con | SD |
| G1 | 15.33 | 1.25 |
| G2 | 63.61 | 1.19 |
| G3 | 120.57 | 1.32 |
| G4 | 44.20 | 1.26 |
| G5 | 28.51 | 1.19 |
| G6 | 16.76 | 1.19 |
FIGURE 7
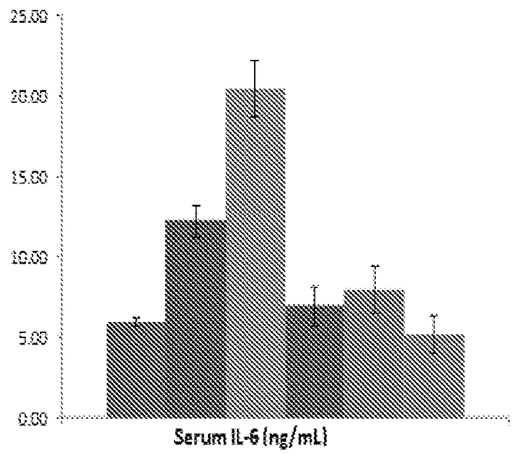
FIGURE 8
| Serum IL-6 (ng/mL) | | |
|---|---|---|
| Group | Mean Con | SD |
| G1 | 5.95231 | 0.24 |
| G2 | 12.23077 | 1.03 |
| G3 | 20.49677 | 1.77 |
| G4 | 6.91643 | 1.18 |
| G5 | 7.96556 | 1.50 |
| G6 | 5.15512 | 1.13 |
FIGURE 9

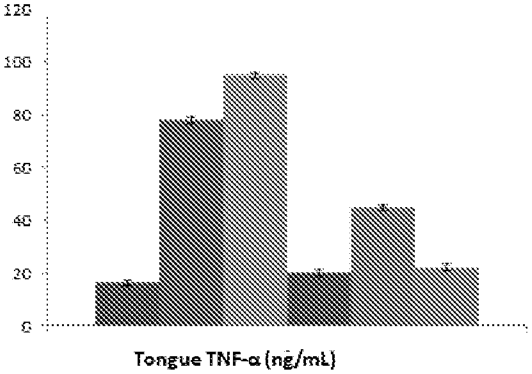
FIGURE 10
| Tongue TNF-α (ng/mL) | | |
|---|---|---|
| Group | Mean Con | SD |
| G1 | 16.27 | 1.19 |
| G2 | 77.96 | 1.48 |
| G3 | 94.88 | 1.17 |
| G4 | 20.07 | 1.13 |
| G5 | 44.76 | 1.02 |
| G6 | 22.16 | 1.29 |
FIGURE 11
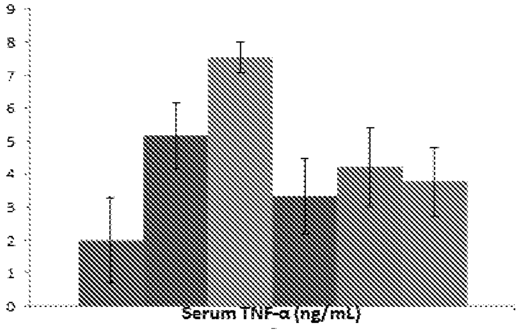
FIGURE 12
| Serum TNF-α (ng/mL) | | |
|---|---|---|
| Group | Mean Con | SD |
| G1 | 1.99 | 1.28 |
| G2 | 5.17 | 1.03 |
| G3 | 7.53 | 0.47 |
| G4 | 3.32 | 1.16 |
| G5 | 4.21 | 1.19 |
| G6 | 3.76 | 1.06 |
FIGURE 13

| Time (h)/ Parameter | Group | | | |
|---|---|---|---|---|
| | G-I | | G-II | |
| | Mean | SD | Mean | SD |
| 0.25 | Not Defined (ND) | ND | ND | ND |
| 0.5 | ND | ND | ND | ND |
| 1 | ND | ND | ND | ND |
| 2 | ND | ND | ND | ND |
| 4 | ND | ND | ND | ND |

| Time (h)/ Parameter | Group | | | | | |
|---|---|---|---|---|---|---|
| | G-I | | G-II | | G-III | |
| | Mean | SD | Mean | SD | Mean | SD |
| **0.25** | 1.8 | 0.5 | - | - | 16.8 | 21.2 |
| **0.5** | 2.1 | 0.3 | - | - | - | - |
| **1** | - | - | 28.3 | 11.0 | 833.6 | 159.2 |
| **4** | 999.8 | 1097.3 | 4.7 | 3.5 | 7.4 | 8.8 |

FIGURE 17

| Pharmacokinetic parameter | Group | | | | | |
|---|---|---|---|---|---|---|
| | G-I | | G-II | | G-III | |
| | Mean | SD | Mean | SD | Mean | SD |
| **$C_{max}$ (ng/mL)** | 999.8 | 1097.2 | 33.4 | 11.0 | 773.1 | 159.3 |
| **$T_{max}$ (h)** | 4.0 | 0.0 | 1.0 | 0.0 | 1.0 | 0.0 |
| **Area Under the Curve (AUC) (ng*h/ml)** | 1754.8 | 1919.2 | 43.0 | 17.3 | 520.2 | 265.4 |

FIGURE 18

| **Pack** | **Assay** | **Percentage stability at time intervals** | |
|---|---|---|---|
| | | **1 month** | **3 months** |
| **Aluminum tube with crimp seal** | Accelerated conditions (40°C± 2°C / 75% ± 5% relative humidity) | 72.7% | 74.2% |
| | Long-term conditions (25⁰C/60% relative humidity) | - | 99.9% |

FIGURE 19

TOPICAL GEL FORMULATION FOR SKIN AND MOUTH DISORDERS AND A PROCESS OF PREPARATION THEREOF

PRIORITY CLAIM

The application claims priority from the provisional specification numbered 202141058855 filed with the Indian Patent Office, Chennai on 17 Dec. 2021 entitled "A topical gel formulation for skin and mouth disorders and a process of preparation thereof", the entirety of which is expressly incorporated herein by reference.

DESCRIPTION OF THE INVENTION

Technical Field of the Invention

The present invention discloses a formulation of a topical or oromucosal gel for the treatment of disorders of the skin and mucus membrane of the oral cavity. More specifically, the formulation is a single oromucosal gel composition for diseases including oral mucositis and Recurrent Aphthous Stomatitis (RAS). The topical or oromucosal gel formulation is further used for the treatment of diabetes foot ulcers, decubitus ulcers, and skin burns. The present invention also discloses a process for the preparation of the topical or oromucosal gel formulation.

BACKGROUND OF THE INVENTION

Aggressive treatment of malignant diseases tends to produce inevitable toxicities to normal cells. The mucosal lining of the gastrointestinal tract is the prime target for toxicity due to the treatment modalities. The oral cavity is highly susceptible to direct and indirect toxic effects of cancer chemotherapy and ionizing radiation.

The radiation-induced oral mucositis is a major toxicity observed in head and neck cancer patients caused by radiotherapy. The radiation-induced oral mucositis has adverse effects on patient's quality of life and cancer therapy continuity. It is also a challenge for radiation oncologists since it leads to cancer therapy interruption.

Oral mucositis begins as an acute inflammation of the oral mucosa, tongue, and pharynx after exposure to radiation. Oral mucositis induces pain, inability to eat, weight loss, and local infection. The inflammation leads to the recruitment of various inflammatory cells and the release of inflammatory cytokines, chemotactic mediators, and growth factors. The ill effects of radiation-induced oral mucositis are life-threatening.

Oral mucositis is also a complication of cancer chemotherapy, which causes the mucosal lining of the mouth to atrophy and break down, and forms ulcers. The risk factors of oral mucositis include the type of tumor-associated, age, oral hygiene, nutritional condition, liver, and kidney function of the individual.

Head and neck radiation are prone to cause a wide range of oral complications. Head and neck radiation induce damage to the vasculature, connective tissue, salivary glands, muscle, and bone.

About 40% of the patients treated with chemotherapy and about 90% of head and neck cancer patients treated with both chemo- and radiotherapy develop mucositis.

Recurrent Aphthous Stomatitis (RAS) is a common disease of the oral mucosa. RAS, also known as canker sores, is often characterized by recurrent painful ulcerations. The factors affecting RAS are nutritional deficiencies, genetic factors, viral and bacterial infections, immune and endocrine disturbances. However, the first line of treatment for RAS involves the recommendation of topical corticosteroids.

Minor canker sores usually subside within 2 weeks without scarring or getting infected. Major canker sores can last up to 1-4 months with recurrent episodes causing extensive scarring. Herpetiform canker sores are clusters of sores that merge to form irregular ulcers. Herpetiform canker sores heal over a period of 10 days. Over several years, topical corticosteroids have been applied for RAS yet lack efficacy in reducing the frequency and systemic interventions. Decubitus ulcers are formed due to pressure exerted on the skin for a prolonged duration. They are most commonly known as bedsores or pressure ulcers. Generally, pressure ulcers develop on skin that covers bony areas of the body. Risk factors include a poor diet, dehydration, diabetes etc. These ulcers cause discoloration of the skin, pain, and infection. There is no fixed treatment regime for decubitus ulcers. The main goals for the treatment of decubitus ulcers are decreasing pressure, preventing additional ulcers, wound management, and appropriate nutrition or surgical intervention.

Diabetic foot ulcers are chronic in nature. These ulcers occur due to increased pressure and hence result in limited blood flow. The pressure cuts off blood supply to the skin and injures the surrounding cells. Initially, the skin usually looks red or a bit discolored. Eventually, if the pressure is not relieved, the skin breaks down and the tissue becomes necrotic.

Skin burns relate to underlying skin tissue damage by chemicals, heat, electricity and radiation. There are three different degrees of skin burn. The degree of burn determines the depth of burn and the amount of affected skin. The first and second-degree burns heal over two to three weeks of proper treatment whereas the third-degree burns are deep and affect a large portion of the skin. They are very serious and can be life-threatening. In order to prevent infection and scarring, all deep burns require treatment.

Misoprostol is characterized as an analog of prostaglandin E1. Misoprostol is used in the prevention of stomach and duodenal ulcers due to different pain medications. Misoprostol decreases the secretion of stomach acid. It decreases ulcer-related complications such as bleeding. Misoprostol has been used for induction of first and second trimester abortion, for induction of labor in the third trimester, and for the control of postpartum hemorrhage. Misoprostol is occasionally used to induce labor and treat ulcers.

The Application No. US2009088366A1 titled "Nitrosated and nitrosylated prostaglandins, compositions and methods of use" discloses a composition of nitrosated and nitrosylated prostaglandins. The composition comprises nitric oxide along with pharmaceutically acceptable salt. The composition comprises phosphodiesterase inhibitor as a vasoactive agent. The composition is administered orally, intracavernosal injection, transurethral application or transdermal application. The invention provides a method for treating and preventing cerebrovascular disorders, cardiovascular disorders, sexual dysfunction in males and females, benign prostatic hyperplasia, inducing abortions, glaucoma and peptic ulcers.

The Application No. US23864694A titled "Method of treating damaged mucosal and epithelial tissues with misoprostol" discloses a composition of misoprostol and a method for treating damaged mucosal and epithelial tissues. The effective amount is about 1 μg to about 1 mg misoprostol per gram of the composition. The method of treatment begins by the cleaning procedure area and topical or oromucosally administering an effective amount of misoprostol.

The calculus from the teeth is removed. The composition comprising 0.004% to 0.1% misoprostol is in the form of a powdered mixture that hydrates upon application to form an adhesive gel. The treatment method disclosed in the composition is effective against periodontal disease and oral ulcers caused by radiation and chemotherapy.

The Application No. US201615151912A1 titled "Novel formulations for the treatment of pain, neuropathy, wounds, and ulcers" discloses a formulation with compounds for the transdermal treatment of pain, neuropathy, wounds and ulcers. The formulation is useful for treating pain, neuropathy and diabetic ulcers in particular. For the treatment of pain and neuropathy, the composition comprises 2% nifedipine and 3% lidocaine in a ratio of 2:3 (w/w). For individualized treatment of neuropathy, the composition additionally comprises Ketamine, amitriptyline, pentoxifylline, mefenamic acid, clonidine and a transdermal and lipodermal base ingredient. For individualized treatment of wounds and ulcers the composition additionally comprises phenytoin, misoprostol, and metronidazole.

The Application No. US61413500A titled "Pharmaceutical tablet comprising an NSAID and misoprostol" discloses a pharmaceutical tablet with Nonsteroidal anti-inflammatory drugs (NSAID) as core and a film coating of polymer and misoprostol. The composition comprises NSAID selected from piroxicam, diclofenac or a salt thereof and the polymer is selected from povidone or hydroxypropyl methylcellulose. The ratio of polymer to misoprostol is about 10:1 to 100:1. The invention discloses a process of making a pharmaceutical composition comprising a core tablet made of NSAID and applying around the core a film coating comprising a polymer and misoprostol by dissolving the polymer and misoprostol in a solvent, spraying the solution on said core, evaporating the solvent and subsequently applying an inert coating to said film coating.

The Application No. WO2008120264A1 titled "Use of misoprostol for the topic treatment of skin lesions by stings and burns" discloses a process for preparation of misoprostol for the treatment of skin lesions from insect bites and stings and superficial burns. The pharmaceutical composition in the form of ointment, cream, gel and paste. Misoprostol is found in the range of 10-25 mg per gram of preparation. Effective amount of misoprostol is applied on surface of the skin with lesions from stings and burns. Misoprostol used as topical or oromucosal ointment, at a high dose, has capability of controlling typical burning pain and of speeding up healing of skin lesions from burns.

Misoprostol has been mainly used for the reduction of peptic ulcers caused by the intake of painkillers. Misoprostol has been occasionally used for treating lesions, burns, wounds and ulcers. Oral mucositis, RAS, diabetes foot ulcers, decubitus ulcers and skin burns can be life threatening if the disease is prolonged and left untreated and the treatment regime is not fixed for these diseases. Hence, there is a need for single product formulation which is safe and effective.

BRIEF DESCRIPTION OF DRAWINGS

FIG. 1 tabulates the composition of topical or oromucosal gel formulation with misoprostol according to an embodiment of the invention.

FIG. 2 tabulates the batch composition of topical or oromucosal gel with misoprostol according to another embodiment of the invention.

FIG. 4 tabulates the oral mucositis scoring criteria.

FIG. 5 illustrates the effect of topical or oromucosal gel formulation in mice with oral mucositis.

FIG. 6 illustrates the tongue Interleukin-6 (IL-6) levels in mice with oral mucositis upon treatment with topical or oromucosal gel formulation.

FIG. 7 tabulates the mean concentration and standard deviation (SD) of tongue IL-6 levels in mice with oral mucositis upon treatment with topical or oromucosal gel formulation.

FIG. 8 illustrates the serum IL-6 levels in mice with oral mucositis upon treatment with topical or oromucosal gel formulation.

FIG. 9 tabulates the mean concentration and standard deviation (SD) of serum IL-6 levels in mice with oral mucositis upon treatment with topical or oromucosal gel formulation.

FIG. 10 illustrates the tongue Tumor Necrosis Factor-α (TNF-α) levels in mice with oral mucositis upon treatment with topical or oromucosal gel formulation.

FIG. 11 tabulates the mean concentration and standard deviation (SD) of tongue TNF-α levels in mice with oral mucositis upon treatment with topical or oromucosal gel formulation.

FIG. 12 illustrates the serum TNF-α levels in mice with oral mucositis upon treatment with topical or oromucosal gel formulation.

FIG. 13 tabulates the mean concentration and standard deviation (SD) of serum TNF-α levels in mice with oral mucositis upon treatment with topical or oromucosal gel formulation.

FIG. 17 tabulates the plasma concentration of misoprostol acid in rats upon intra-gastric administration of the topical or oromucosal gel formulation.

FIG. 17 tabulates the pharmacokinetic parameters of misoprostol acid in rats upon intra-gastric administration of the topical or oromucosal gel formulation.

FIG. 18 tabulates the pharmacokinetic parameters in rats upon intra-gastric administration of the topical or oromucosal gel formation.

FIG. 19 tabulates the stability analysis of packaged topical or oromucosal gel formulation.

SUMMARY OF THE INVENTION

Figure 3:
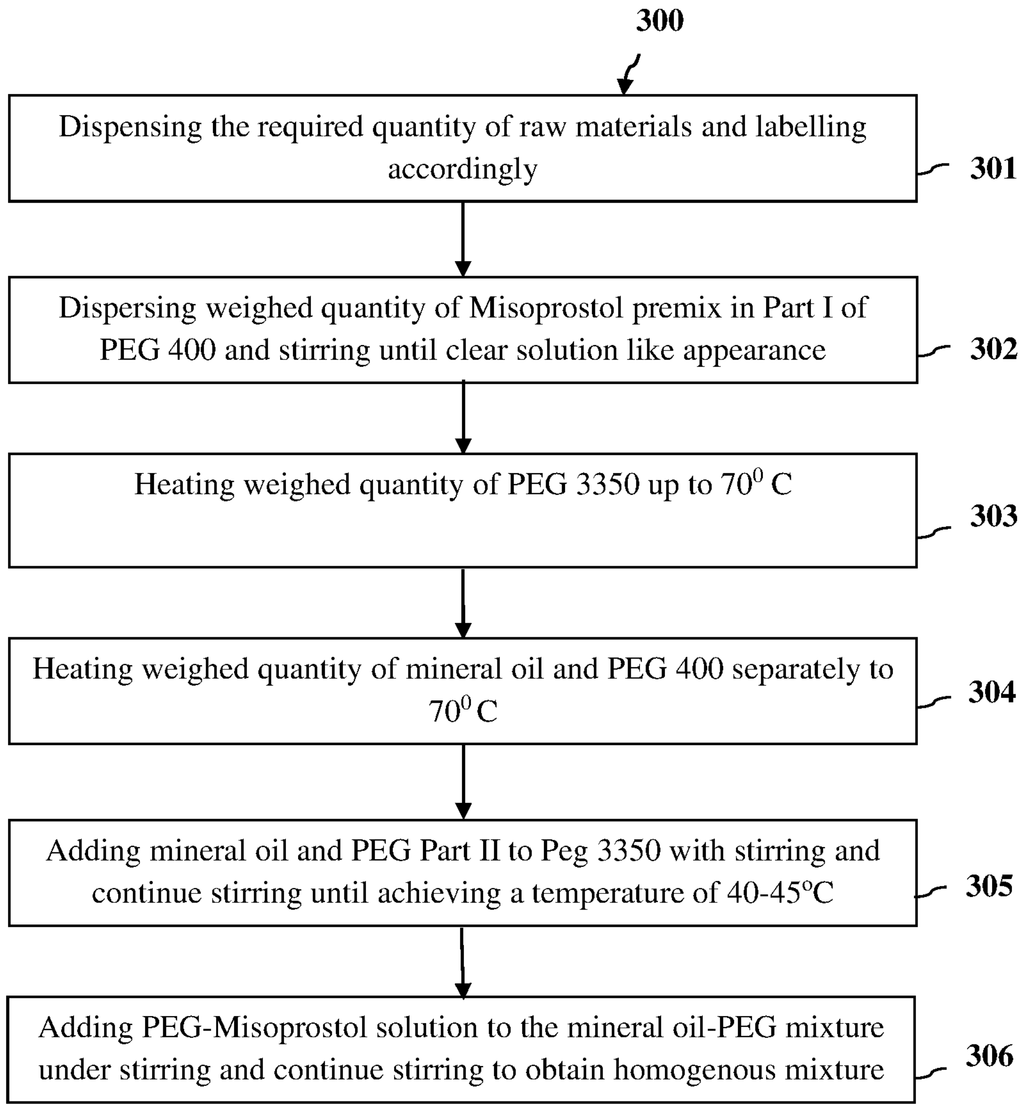
FIG. 3 illustrates flow chart for a process for the preparation of topical or oromucosal gel formulation according to the embodiment of the invention.

The present invention overcomes the drawbacks of the prior arts. The present invention discloses a single topical or oromucosal gel formulation for skin and mouth disorders. The formulation of the present invention is used to treat skin and mouth disorders including oral mucositis, RAS, diabetes foot ulcers, decubitus ulcers and skin burns. The topical or oromucosal gel formulation of the present invention is safe and effective.

The topical or oromucosal gel formulation comprises misoprostol as an active ingredient, mineral oil, Polyethylene Glycol 400-Part-I, PEG 400-Part-II, and PEG 3350. The topical or oromucosal gel formulation exhibits prolonged residence time.

The present invention further discloses the process of preparation of the topical or oromucosal gel formulation. The process begins with measuring required quantities of misoprostol, mineral oil, Polyethylene Glycol 400 (PEG 400), and Polyethylene Glycol 3350 (PEG 3350). The weighed quantity of misoprostol is dispensed in PEG 400. The mineral oil, PEG 400 and PEG 3350 are individually heated to a temperature of 70° C. and mixed with misoprostol with constant stirring to form a homogenous mixture upon cooling.

The topical or oromucosal gel formulation of the present invention has been analyzed for various pharmacological parameters in order to test the safety and efficacy of misoprostol. The parameters such as tongue and serum levels of biomarkers IL-6 and TNF-α, anti-mucositis activity, histopathological studies and body weight are evaluated. The parameters are analyzed in groups of BALB/c male mice.

The analysis of anti-mucositis activity indicates the effect of topical or oromucosal gel formulation against oral mucositis. The topical or oromucosal gel formulation exhibited a significant decrease in oral mucositis. The mucositis score was found to be decreased to zero upon application of topical or oromucosal gel formulation.

The effect of topical or oromucosal gel formulation is further analyzed on the concentration of biomarkers. The concentration of biomarkers including inflammatory cytokines TNF-α and IL-6 significantly decreased upon treatment with topical or oromucosal gel formulation. The histopathological analysis of cheek pouches indicated normal morphology of the cells upon treatment with topical or oromucosal gel formulation.

The pharmacokinetics of the topical or oromucosal gel formulation has been analyzed for oromucosal and intragastric route of administration. The oromucosal route of administration exhibits below the limit quantification of misoprostol acid in plasma and the intra-gastric route of administration exhibits pharmacokinetic parameters including maximum concentration, time and area under the curve at higher concentrations of misoprostol.

The stability of packaged topical or oromucosal gel formulation has been analyzed at accelerated and long-term environmental conditions. The topical or oromucosal gel formulation is packaged in crimp sealed aluminium tubes. Crimp sealed aluminium tubes exhibited assay values of about 99% under long-term storage conditions. The stability data exhibits that the formulation is stable when packaged in aluminum tubes and when stored at simulated room temperature conditions.

The topical or oromucosal gel formulation of the present invention aids in treatment of skin disorders effectively. The topical or oromucosal gel formulation has prolonged residence time, which aids in effective treatment of the skin disorder. The topical or oromucosal gel formulation does not comprise astringents, hence, prevents the cause of skin-related side effects. The topical or oromucosal gel formulation reduces inflammatory biomarkers. The formulation is safe, effective and stable.

DETAILED DESCRIPTION OF THE INVENTION

In order to more clearly and concisely describe and point out the subject matter of the claimed invention, the following definitions are provided for specific terms, which are used in the following written description.

The term "Histopathology" refers to study of cells and tissues under a microscope for diagnosis.

The term "Residence time" refers to the duration in which a molecule stays in the body.

The present invention discloses a formulation of topical or oromucosal gel, which treats disorders of skin and mouth such as oral mucositis, RAS, diabetes foot ulcers, decubitus ulcers, skin burns etc.

The formulation comprises misoprostol as an active ingredient in the form of a topical or oromucosal gel. The invention discloses a topical or oromucosal gel formulation comprising misoprostol, mineral oil, Polyethylene Glycol 400-Part-I, PEG 400-Part-II, and Polyethylene Glycol 3350 (PEG 3350).

The topical or oromcosal gel formulation comprises a locally acting gel composition and is hydrophilic in nature with prolonged residence time at the site of action. The gel comprising various ratios of grades of PEG and mineral oil helps in providing a stable gel base.

The topical or oromucosal gel formulation comprising misoprostol is in the form of 1% dispersion in Hydroxypropyl methylcellulose (HPMC). Misoprostol at higher moisture content is prone to degradation. Hence, in order to avoid the degradation of misoprostol, the manufacturing process does not incorporate the use of water. The use of astringent compounds and alcohol has been avoided in the formulation thus reducing the risk of irritation and burning. Misoprostol is incorporated in the formulation in the form of dispersion and is capable of being incorporated as an oily liquid.

The present invention discloses formulations of two topical or oromucosal gels comprising 100 ug/g of misoprostol drug corresponding to a concentration of 0.01% and 30 ug of misoprostol drug corresponding to a concentration of 0.003% respectively.

FIG. 1 tabulates the composition of topical or oromucosal gel formulation with misoprostol according to an embodiment of the invention. The composition of 0.01% misoprostol topical or oromucosal gel formulation comprises 10 mg/g of 1% (w/w) misoprostol 1% dispersion, which corresponds to 2.5 g per batch, 100 mg/g of 10% mineral oil, which corresponds to 25 g per batch, 100 mg/g of 10% PEG 400-Part I, which corresponds to 25 g per batch, 464.4 mg/g of 26.44%-66.44% of PEG 400-Part II, which corresponds to 116.10 g per batch and 325.60 mg/g of 12.56%-52.56% of PEG 3350, which corresponds to 81.40 g per batch. The composition of 0.003% misoprostol topical or oromucosal gel formulation comprises 3 mg/g of 0.3% (w/w) misoprostol 1% dispersion, which corresponds to 0.75 g per batch, 100 mg/g of 10% mineral oil. Which corresponds to 25 g per batch, 100 mg/g of 10% PEG 400-Part I which corresponds to 25 g per batch, 464.4 mg/g of 26.46%-66.44% PEG 400-Part II which corresponds to 116.10 g per batch and 332.60 mg/g of 13.26%-53.26% PEG 3350 which corresponds to 83.15 g per batch.

Misoprostol is dispersed in PEG 400 to ensure uniform distribution of the drug. The present invention further discloses a process for preparation of topical or oromucosal gel formulation.

FIG. 3 illustrates flow chart for the process of preparation of topical or oromucosal gel formulation according to an embodiment of the invention. The process (300) starts with a step (301) of dispensing the required quantity of raw materials and labelling. At step (302), misoprostol premix is dispersed in Part I of PEG 400 and stirred until clear solution like appearance is achieved. At step (303), weighed quantity of PEG 3350 is heated up to 70° C. At step (304), mineral oil and PEG 400 are heated separately to 70° C. At step (305), mineral oil and PEG Part II are added to Peg 3350 with stirring and continuing to stir until a temperature of 40-45° C. is achieved. At step (306), PEG-misoprostol solution is added to the mineral oil-PEG mixture under stirring and continued to stir until homogenous mixture is obtained.

The following examples are offered to illustrate various aspects of the invention. However, the examples are not intended to limit or define the scope of the invention in any manner.

Example 1: Batch Composition of Topical or Oromucosal Gel of Misoprostol

The invention discloses a composition of topical or oromucosal gel formulation comprising misoprostol drug at a concentration of 0.01% and 0.003% respectively.

FIG. 2 tabulates the batch composition of topical or oromucosal gel with misoprostol according to another embodiment of the invention. The composition of 0.01% misoprostol topical or oromucosal gel formulation comprises 1 g/100 g of 1% (w/w) misoprostol 1% dispersion which corresponds to 2.5 g per batch, 10 g/100 g of 10% mineral oil which corresponds to 25 g per batch, 10 g/100 g of 10% PEG 400-Part I which corresponds to 25 g per batch, 46.44 g/100 g of 26.44%-66.44% PEG 400-Part II which corresponds to 116.10 g per batch and 32.56 g/100 g of 32.56% PEG 3350 which corresponds to 81.40 g per batch. The composition of 0.003% misoprostol topical or oromucosal gel formulation comprises 0.3 g/100 g of 0.3% (w/w) misoprostol 1% dispersion which corresponds to 0.75 g per batch, 10 g/100 g of 10% mineral oil which corresponds to 25 g per batch, 100 mg/g of 10% PEG 400-Part I which corresponds to 25 g per batch, 46.44 g/100 g of 26.44%-66.44% of PEG 400-Part II which corresponds to 116.10 g per batch and 33.26 g/100 g of 13.26%-53.26% PEG 3350 which corresponds to 83.15 g per batch.

The topical or oromucosal gel formulation of the present invention has been analyzed for various pharmacological parameters in order to test the safety and efficacy of misoprostol. The parameters such as tongue and serum levels of biomarkers IL-6 and TNF-α, anti-mucositis activity, histopathological studies and bodyweight have been evaluated in male BALB/c mice.

The in vivo pharmacological assessment of anti-mucositis activity of the topical or oromucosal gel formulation in male BALB/c mice was performed. The study protocol involves six BALB/c mice namely vehicle, 5-Fluorouracil (FU) group, 5 FU-group+Scratching, FU-group+Scratching, FU-group+Scratching+100 ug gel and FU-group+Scratching+30 ug respectively were maintained under specific pathogen-free conditions. The mice were 6-8 weeks of age and weighed 25-30 g. All animal experimental procedures were performed in accordance with the Institutional Animal Ethics Committee (IAEC) guidelines along with approval from IAEC.

Example 2: Efficacy of the Topical or Oromucosal Gel Formulation with Misoprostol in Mice with Oral Mucositis The activity of misoprostol of the topical or oromucosal gel formulation was analyzed for anti-mucositis in mice. The anti-mucositis activity is analyzed based on the mucositis score. The scoring parameters for anti-mucositis activity include erythema, vasodilation, erosion, bleeding, fibrosis, and ulcers.

A scoring method is adopted for oral mucositis induced by radiation and chemotherapy. The scoring evaluates the relationship between dosage, delivery method and complications. The Scoring systems are useful in assessing the impact of therapy on patient.

FIG. 4 tabulates the oral mucositis scoring criteria. Scoring is given from 0 to 5 where 0 being regarded as completely healthy and 5 being regarded as completely ulcerated.

The anti-mucositis study protocol involves mice that are intraperitoneally administered with 5-FU at 100 mg/kg on day 0. The scratching group of mice was anesthetized with isoflurane and an area of 0.5 $cm^2$ of the tongue was scratched using the tip of an 18-gauge needle at an equal force and depth on days 7 and 8. The scratching was blinded to the treatment groups. Dexamethasone was administered orally at 1 mg/kg/day from on day 7.

FIG. 5 illustrates the effect of topical or oromucosal gel formulation in mice with oral mucositis. The mucositis score was evaluated for 6 groups of mice (G1-G6) over a period of 15 days. The G1 (saline) group exhibited 0 mucositis score. The G2 (5-FU) group had a mucositis score of 0 for 8 days and a mucositis score of 1 for the remaining 7 days. The G3 (5-FU+Scratch) group exhibited increase in mucositis score till day 8 and maintained a mucositis score of 3 for remaining 7 days. The G4 (5-FU+Scratch+Dexamethasone) group exhibited a similar trend to G3 where the mucositis score steadily increased to 3 till day 8 and gradually decreased to 1 over the remaining 7 days. The G5 (5-FU+Scratch+30 ug gel) exhibited very similar trend to G4 where the mucositis score steadily increased to 3 till day 8 and gradually decreased to slightly more than 1 over the remaining 7 days. The G5 (–FU+Scratch+100 ug gel) exhibited a steady increase of mucositis score to 3 over a period of 9 days and gradually the mucositis score decreased to zero over the remaining 6 days.

The biomarkers such as IL-6, IL-1B, TNF-α etc. come under the class of "cytokines" which play a variety of functions mainly as inflammatory markers. These biomarkers are mainly evaluated in order to assess the immune response of the organism to the drug. The elevated levels of these biomarkers suggest an aggravated immune response by the organism. These biomarkers regulate the immune response in an organism.

The levels of biomarkers such as IL-6 and TNF-α were analyzed in mice upon treatment with topical or oromucosal gel formulation. The concentrations of these biomarkers in serum and tongue were analyzed using standard ELISA kits.

Example 3: Analysis of Effect on IL-6 Concentrations on Mice Upon Treatment with Topical or Oromucosal Gel Formulation The tongue and serum concentrations of IL-6 were analyzed in mice with oral mucositis upon treatment with topical or oromucosal gel formulation. The concentrations of IL-6 in tongue and serum were analyzed using mouse IL-6 ELISA kit.

FIG. 6 illustrates the tongue IL-6 levels in mice with oral mucositis upon treatment with topical or oromucosal gel formulation. The G1 group exhibits the least mean concentration of 15.33, G2 group exhibits a mean concentration of 63.61, G3 group exhibits a mean concentration of 120.57, G4 group exhibits mean concentration of 44.20, G5 group exhibits mean concentration of 28.21 and G6 group exhibits mean concentration of 16.76.

FIG. 7 tabulates the mean concentration and standard deviation (SD) of tongue IL-6 levels in mice with oral mucositis upon treatment with topical or oromucosal gel formulation.

FIG. 8 illustrates the serum IL-6 levels in mice with oral mucositis upon treatment with topical or oromucosal gel formulation. The G1 group exhibits the least mean concentration of 5.95, G2 group exhibits a mean concentration of 12.23, G3 group exhibits a mean concentration of 20.5, G4 group exhibits mean concentration of 6.91, G5 group exhibits mean concentration of 7.97 and G6 group exhibits mean concentration of 5.16.

FIG. 9 tabulates the mean concentration and standard deviation (SD) of serum IL-6 levels in mice with oral mucositis upon treatment with topical or oromucosal gel formulation.

Example 4: Analysis of Effect on TNF-α Concentrations in Mice Upon Treatment with Topical or Oromucosal Gel Formulation The tongue and serum concentrations of TNF-α were analyzed in mice with oral mucositis upon treatment with topical or oromucosal gel formulation. The concentrations of TNF-α in tongue and serum were analyzed using mouse TNF-α ELISA kit.

FIG. 10 illustrates the tongue TNF-α levels in mice with oral mucositis upon treatment with topical or oromucosal gel formulation. The G1 group exhibits the least mean concentration of 16.27, G2 group exhibits a mean concentration of 77.96, G3 group exhibits a mean concentration of 94.88, G4 group exhibits mean concentration of 20.07, G5 group exhibits mean concentration of 44.76 and G6 group exhibits mean concentration of 22.16.

FIG. 11 tabulates the mean concentration and standard deviation (SD) of tongue TNF-α levels in mice with oral mucositis upon treatment with topical or oromucosal gel formulation.

FIG. 12 illustrates the serum TNF-α levels in mice with oral mucositis upon treatment with topical or oromucosal gel formulation. The G1 group exhibits the least mean concentration of 1.99, G2 group exhibits a mean concentration of 5.17, G3 group exhibits a mean concentration of 7.53, G4 group exhibits mean concentration of 3.32, G5 group exhibits mean concentration of 4.21 and G6 group exhibits mean concentration of 3.76.

FIG. 13 tabulates the mean concentration and standard deviation (SD) of serum TNF-α levels in mice with oral mucositis upon treatment with topical or oromucosal gel formulation.

The histopathological analysis involves examining tissues or cells under a microscope, which provides detailed understanding of mechanism and progression of the disease.

Example 5: Analysis of Histopathology of Cheek Pouches of Mice with Oral Mucositis Upon Treatment with Topical or Oromucosal Gel Formulation The histopathology of cheek pouches of mice with oral mucositis was performed. The histopathology of cheek pouches with oral mucositis were analyzed by 100-X light microphotographs of first treated animal of post treated mice groups.

Figure 14:
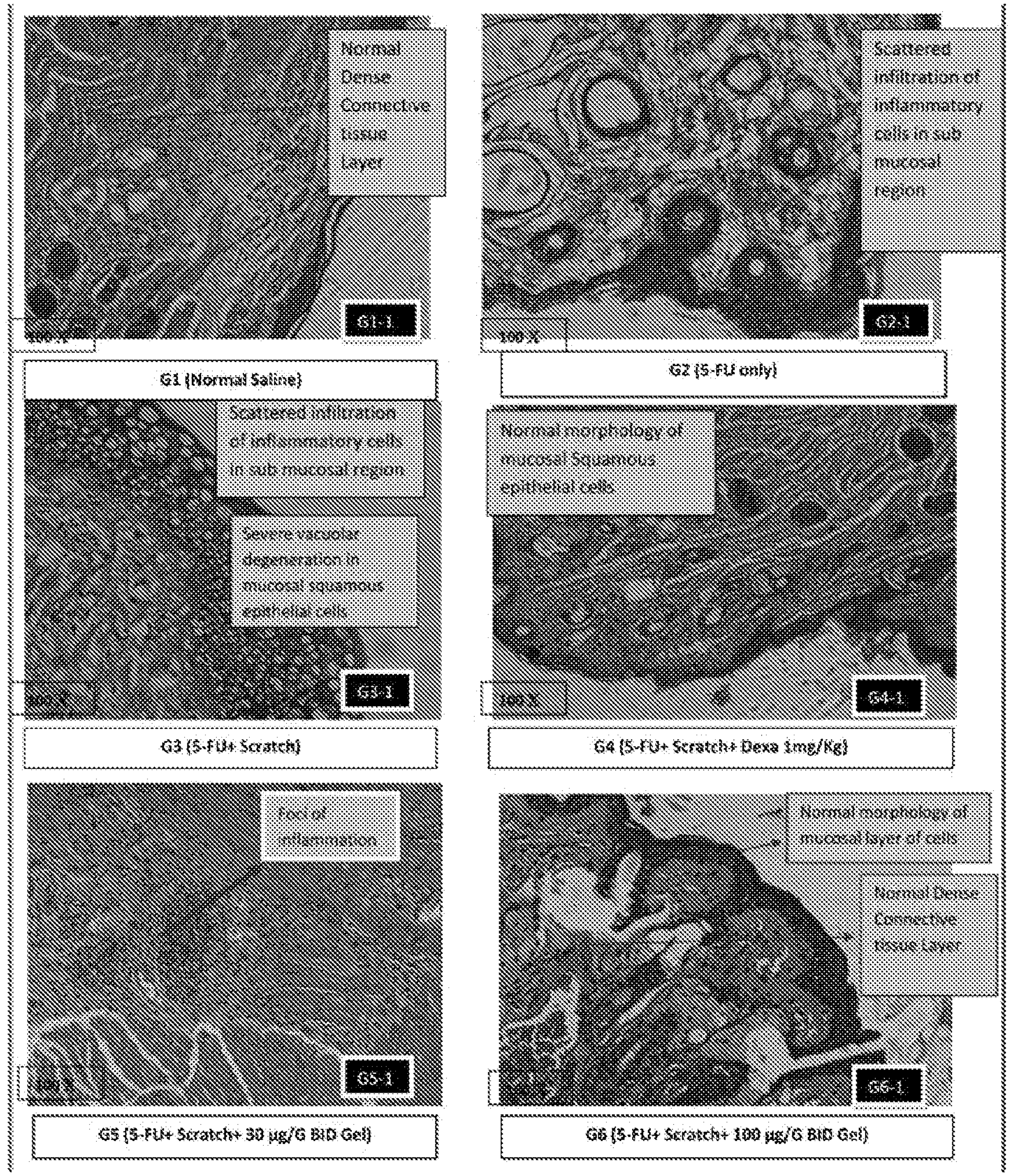
FIG. 14 illustrates the microscopic images of cheek pouches of mice with oral mucositis upon treatment with topical or oromucosal gel formulation.

FIG. 14 illustrates the microscopic images of cheek pouches of mice with oral mucositis upon treatment with topical or oromucosal gel formulation. The G1 group exhibits normal histopathology with normal dense connective tissue layer. The G2 group exhibits a histopathology of scattered infiltration of inflammatory cells in sub-mucosal layer. The G3 group exhibits a histopathology of scattered infiltration of inflammatory cells in sub-mucosal layer along with severe vacuolar degeneration in mucosal squamous epithelial cells. The G4 group exhibits a histopathology of normal morphology of mucosal squamous epithelial cells. The G5 group exhibits a pathology where the foci of inflammation are observed. The G6 group exhibits a pathology where normal morphology of mucosal layer of cells along with normal dense connective tissue are observed.

The effect of drug on the body weight of the organism is usually studied to determine the safety and efficacy of the drug. Any significant increase of decrease in weight determines variation in metabolism of the organism due to the effect of the drug.

Example 6: Analysis of Body Weights of Mice with Oral Mucositis Upon Treatment with Topical or Oromucosal Gel Formulation The body weights of mice with oral mucositis upon treatment with topical or oromucosal gel formulation were analyzed for a period of 15 days.

Figures 15, 16:
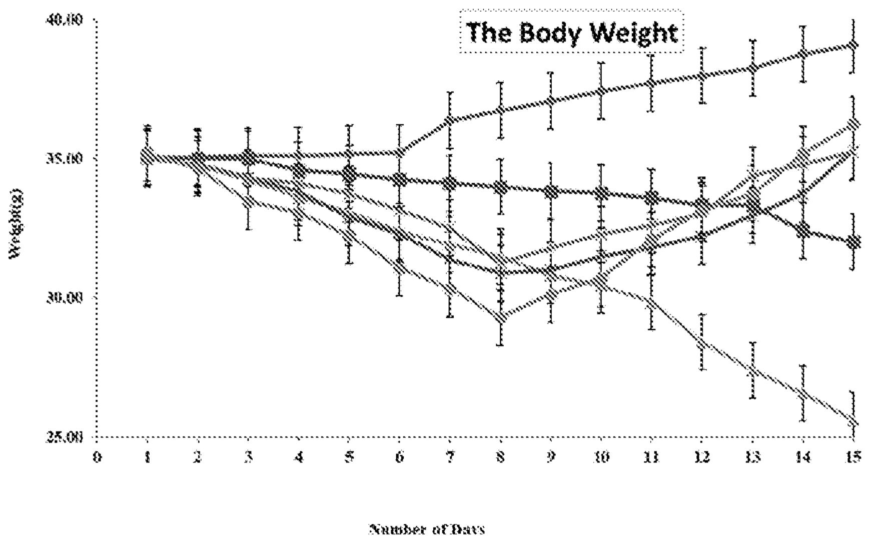
FIG. 15 illustrates the effect on body weight of mice with oral mucositis upon treatment with topical or oromucosal gel formulation.
FIG. 16 tabulates the plasma concentration of misoprostol acid in rats upon oromucosal administration of the topical or oromucosal gel formulation.

FIG. 15 illustrates the body weight of mice with oral mucositis upon treatment with topical or oromucosal gel formulation. The G1 group exhibits a steady increase of weight to 40 g over a period of 15 days. The G2 group exhibits slight decrease in weight over a period of 15 days. The G3 group exhibits steady decrease in weight to 25 g over a period of 15 days. The G4 exhibits decrease in weight for 8 days and gradually increases over the remaining 7 days. The G5 group exhibited similar trend to that of G4 where the weight gradually decreased for 8 days and increased over the remaining 7 days. The G6 group exhibited a steady decrease in weight for 8 days and a steady increase in weight for the remaining 7 days.

The topical or oromucosal gel formulation was subjected to pharmacokinetic analysis to analyze the effect of oromucosal application. The pharmacokinetic analysis aids in optimizing the dosage guidelines and regimes of the formulation. Further, the interaction of molecules is assessed through pharmacokinetic analysis.

The pharmacokinetics of topical or oromucosal gel formulation was analyzed for oromucosal and intra-gastric route of administration. The pharmacokinetics of the topical or oromucosal gel formulation was analyzed in male rats (*Rattus norvegicus*) of 12-14 weeks age and weighing 250-300 g. The rats were subjected to controlled environmental conditions of 20° C.-25° C., relative humidity of 30-70%, a light and dark cycle of 12 hours and 15-20 fresh air changes per hour in a sterile polycarbonate rat cage. The rats were acclimatized for 7 days prior to pharmacokinetic analysis of the topical or oromucosal gel formulation.

Example 7: Pharmacokinetic Analysis of Oromucosal Application of Topical or Oromucosal Gel Formulation The pharmacokinetics of oromucosal application of topical or oromucosal gel formulation was evaluated to analyze the bioavailability of the formulation. The dosage regimen of topical or oromucosal gel formulation administered through oromucosal route was 100 μg/kg administered in the morning and in the evening. The pharmacokinetics of the topical or oromucosal gel formulation was evaluated on 2 groups of rats comprising 12 rats in each group. The first group of rats were administered with 50 μg/kg of the topical or oromucosal gel formulation and the second group of rats were administered with 100 μg/kg of the topical or oromucosal gel formulation.

The pharmacokinetics involved analysis of the blood samples collected at regular intervals of 0.25 hours, 0.5 hours, 1 hour, 2 hours and 4 hours. The collected blood samples were centrifuged at 4000 rpm for 10 minutes to obtain the plasma sample. The obtained plasma samples were subjected to liquid chromatography-mass spectrometry (LC-MS) analysis to analyze the absorption of topical or oromucosal gel formulation and to detect the presence of metabolites including misoprostol acid of the topical or oromucosal gel formulation.

FIG. 16 tabulates the plasma concentration of misoprostol acid in rats upon oromucosal administration of the topical or oromucosal gel formulation. The LC-MS analysis of the plasma samples indicates below the limit quantification of misoprostol acid in the plasma. The mean and standard deviation cannot be determined for the plasma concentration of misoprostol acid in both the groups of rats. The absence of misoprostol acid in plasma indicates that misoprostol of the topical or oromucosal gel formulation has not been significantly absorbed by the oral mucosal cavity and the metabolite has not been found in the systemic circulation. The reduced systemic absorption of the topical or oromucosal gel formulation essentially decreases the toxicity and the adverse effects of the topical or oromucosal gel formulation. The study further indicates that the oromucosal administration of the topical or oromucosal gel formulation has a significant local effect in the oromucosal cavity.

Example 8: Pharmacokinetic Analysis of Intra-Gastric Administration of Topical or Oromucosal Gel Formulation The pharmacokinetics of misoprostol acid metabolite upon oral or intragastric administration of the topical or oromucosal gel formulation were determined to evaluate the systemic absorption of misoprostol. The topical or oromucosal gel formulation was dissolved in saline and administered as a single dose, while misoprostol (pure API) dissolved in saline as served as a positive control. The gel formulation was dosed in 2 groups of rats (G-II and G-III) comprising 3 rats in each group. The group (G1) was administered with 0.2 mg/kg of the drug (Pure API), the second group (G-II) was administered with 50 μg/kg of the topical or oromucosal gel formulation, and the third group (G-III) was administered with 100 μg/kg of the topical or oromucosal gel formulation.

The pharmacokinetics involved analysis of the blood samples collected at regular intervals of 0.25 hours, 0.5 hours, 1 hour and 4 hours. The obtained plasma samples were subjected to liquid chromatography-mass spectrometry (LC-MS) analysis to analyze the absorption of topical or oromucosal gel formulation and to detect the presence of metabolites including misoprostol acid of the topical or oromucosal gel formulation.

FIG. 17 tabulates the plasma concentration of misoprostol acid in rats upon intra-gastric administration of the topical or oromucosal gel formulation. FIG. 18 tabulates the pharmacokinetic parameters in rats upon intra-gastric administration of the topical or oromucosal gel formulation. The mean maximum plasma concentration of misoprostol acid observed in G-I rats was found to be 999.8 ng/ml and the standard deviation was found to be 1097.2 ng/ml. The mean maximum time observed in G-I rats was found to be at 4.0 hours and the mean area under the curve was found to be 1754.8 ng*h/ml and the standard deviation was found to be 1919.2 ng*h/ml. The mean maximum plasma concentration of misoprostol acid observed in G-II rats was found to be 33.4 ng/ml and the standard deviation was found to be 11.0 ng/ml. The mean maximum time observed in G-II rats was found to be at 1.0 hours and the mean area under the curve was found to be 43.0 ng*h/ml and the standard deviation was found to be 17.3 ng*h/ml. The mean maximum plasma concentration of misoprostol acid observed in G-III rats was found to be 773.1 ng/ml and the standard deviation was found to be 159.3 ng/ml. The mean maximum time observed in G-III rats was found to be at 1.0 hours and the mean area under the curve was found to be 520.2 ng*h/ml and the standard deviation was found to be 265.4 ng*h/ml.

The presence of misoprostol acid, a metabolite of misoprostol topical or oromucosal gel formulation indicates significant absorption, of drug from the gel formulation when administered orally, into the systemic circulation.

The process of preparation of topical or oromucosal gel formulation is followed by packaging the gel formulation in to bottles and tubes. The stability analysis is crucial for determining optimal storage conditions, quality, and shelf-life. The packaged topical or oromucosal gel formulation was tested for stability at time intervals of 1 month and 3 months.

Example 9: Stability Analysis of Topical or Oromucosal Gel Formulation

The topical or oromucosal gel formulation was subjected to packaging in crimp sealed aluminium tubes. The stability analysis was conducted for accelerated and long-term conditions. The topical or oromucosal gel formulation was subjected to accelerated condition of 75% relative humidity at 40° C. and long-term condition of 60% relative humidity at 250° C. stored at ambient conditions. The packaged topical or oromucosal gel formulation was analyzed for assay of Misoprostol under accelerated conditions at time intervals of 1 month and 3 months. The topical or oromucosal gel formulation was analyzed for stability under long-term conditions at time interval of 3 months.

FIG. 19 tabulates the stability analysis of packaged topical or oromucosal gel formulation. The crimp sealed aluminium tubes exhibited assay values of about 99% under long-term storage conditions. The topical or oromucosal gel formulation is stable when packaged in aluminum tubes and when stored at simulated room temperature conditions.

Among the various parameters analyzed on mice, misoprostol is found to be safe and effective. The analysis of anti-mucositis activity suggests that the mice treated with misoprostol has least oral mucositis score, which corresponds to the positive effect of misoprostol on oral mucositis. The analysis serum and tongue concentrations of biomarkers such as IL-6 and TNF-α in mice exhibits a decrease in concentration which does not indicate any abnormal immune response due to misoprostol in mice. The histopathology of cheek pouch of mice treated with misoprostol suggests reduction of inflammatory activity along with normal cell characteristics upon treatment with misoprostol. The body weight of mice treated with misoprostol shows regain of normal weight which indicates misoprostol is safe and efficacious.

The present invention discloses a formulation of topical or oromucosal gel for the treatment of skin and mouth disorders. The formulation of the present invention is effective as a single gel composition against oral mucositis, RAS, diabetes foot ulcers, decubitus ulcers and skin burns. The animal studies indicate that upon administering the formulation at different doses the oral mucositis score reduced significantly. The concentration of the biomarkers IL-6 and TNF-α also reduced after administration of the drug. The histopathology of cheek pouch of mice suggests that the mucositis affected tissue has regained normalcy upon administration of the drug. The topical or oromucosal gel formulation is self-administered once or twice per day by the patient. The topical or oromucosal gel formulation has prolonged residence time, which aids in presence of drug for longer duration action at the site of action. The formulation does not contain alcohol or any astringent compounds to prevent irritation and burning. The formulation of the present invention has desirable consistency and spread ability. The topical or oromucosal gel formulation of the present invention is stable under accelerated and long-term conditions.

We claim:

1. A topical or oromucosal gel formulation for treatment of skin and mouth disorders, the formulation comprising:

a) a misoprostol dispersion at a concentration range of 0.003%-0.01% (w/w);

b) a mineral oil at a concentration of 10% (w/w);

c) a polyethylene glycol (PEG) 400 Part I at a concentration of 10% (w/w);

d) a PEG 400 Part II at a concentration range of 26.44%-66.44% (w/w);

e) a PEG 3350 at a concentration range of 12.56%-52.56% (w/w).

2. The topical or oromucosal gel formulation as claimed in claim 1, wherein said skin and mouth disorders are oral mucositis, Recurrent aphthous stomatitis (RAS), diabetes foot ulcers, decubitus ulcers and skin burns.

3. The topical or oromucosal gel formulation as claimed in claim 1, wherein said topical or oromucosal gel formulation reduces the concentration of inflammatory biomarkers Tumor Necrosis Factor-α (TNF-α) and Interleukin-6 (IL-6) in serum and tongue of mouse.

4. The topical or oromucosal gel formulation as claimed in claim 1, wherein said topical or oromucosal gel formulation is packaged into crimp sealed aluminum tubes.

5. A process of preparation of topical or oromucosal gel formulation, the process comprising the steps of:

a) measuring 0.003%-0.01% (w/w) of misoprostol, 10% (w/w) of mineral oil, 10% (w/w) of PEG 400 Part-I, 26.44%-66.44% (w/w) of PEG 400 Part-II, and 12.56%-52.56% (w/w) of PEG 3350;

b) dispersing 0.003%-0.01% (w/w) misoprostol in PEG 400 Part-I and stirring to obtain a clear solution;

c) subjecting PEG 3350 to heating;

d) subjecting mineral oil and PEG 400 Part-II separately to heating;

e) mixing mineral oil and PEG 400 Part-II and PEG 3350 with constant stirring; and f) subjecting misoprostol-PEG 400 Part-I solution and mineral oil-PEG mixture to constant stirring.

6. The process as claimed in claim 5, wherein said PEG 3350 is heated to a temperature of 70° C.

7. The process as claimed in claim 5, wherein said mineral oil and PEG 400 Part-II are heated to a temperature of 70° C.

8. The process as claimed in claim 5, wherein subjecting said mineral oil and PEG 400 Part-II to separate heating to enhance the miscibility with PEG 3350.

9. The process as claimed in claim 5, wherein said PEG 400 Part-II and PEG 3350 are stirred maintaining a temperature range of 40° C.-45° C.

* * * * *